United States Patent [19]
Fujisawa et al.

[11] Patent Number: 5,716,206
[45] Date of Patent: Feb. 10, 1998

[54] APPARATUS FOR HEATING A WIRE CONNECTION OR CONNECTOR

[75] Inventors: Atsushi Fujisawa; Akihiro Komori; Shigeki Furukawa, all of Yokkaichi, Japan

[73] Assignee: Sumitomo Wiring Systems, Ltd., Japan

[21] Appl. No.: 575,348

[22] Filed: Dec. 20, 1995

[30] Foreign Application Priority Data

Jan. 5, 1995 [JP] Japan .................. 7-00265
Jan. 5, 1995 [JP] Japan .................. 7-00266

[51] Int. Cl.$^6$ .................................................. F27B 9/14
[52] U.S. Cl. ...................... 432/122; 432/231; 219/388
[58] Field of Search ........................... 228/105, 179.1; 174/17.08; 219/388, 524, 525, 535; 432/59, 8, 122, 231

[56] References Cited

U.S. PATENT DOCUMENTS

| | | |
|---|---|---|
| 2,821,146 | 1/1958 | Mahrle et al. . |
| 3,476,889 | 11/1969 | Belcher et al. . |
| 3,563,202 | 2/1971 | Mackrael et al. .......... 219/388 |
| 3,772,481 | 11/1973 | Saponaro . |
| 4,155,435 | 5/1979 | Kimura et al. . |
| 4,227,596 | 10/1980 | Bartels . |
| 4,271,330 | 6/1981 | Watine et al. . |
| 4,283,596 | 8/1981 | Vidakovits et al. . |
| 4,375,195 | 3/1983 | Tsuboi . |
| 4,400,592 | 8/1983 | Ross, Sr. . |
| 4,418,251 | 11/1983 | Hartman et al. . |
| 4,428,466 | 1/1984 | Mayer . |
| 4,550,231 | 10/1985 | Ross, Sr. . |
| 4,832,248 | 5/1989 | Soni et al. . |
| 5,449,056 | 9/1995 | Ross . |
| 5,503,259 | 4/1996 | Clopton et al. . |

FOREIGN PATENT DOCUMENTS

WO 90/07202  6/1990  WIPO .

*Primary Examiner*—Henry A. Bennett
*Assistant Examiner*—Jiping Lu
*Attorney, Agent, or Firm*—Anthony J. Casella; Gerald E. Hespos; Ludomir A. Budzyn

[57] ABSTRACT

A heating apparatus 1 includes a plurality of closable heating units 10 arranged at specified intervals and each provided with a heater 14, a conveyor 20 for conveying the closable heating units 10 along a loop-shaped conveyance path including a setting station 31, an unloading station 32 and a cooling station 33, and a controller for controlling the heater 14 to heat a solder containing wire connector set in the heating unit at the setting station 31 until the heating unit sent out from the setting station 31 reaches the cooling station 33. The heating apparatus 1 thus constructed heats a wire connection, in particular a connector, such that the wire connection is secure and watertight, and has a good working efficiency.

11 Claims, 9 Drawing Sheets

APPARATUS FOR HEATING A WIRE CONNECTION OR CONNECTOR

BACKGROUND OF THE INVENTION

1. Field of the Invention

The present invention relates to an apparatus for heating a wire connection or connector.

2. Description of the Prior Art

When wires having their insulating sheaths peeled off at at least one of their leading ends are to be electrically connected, a solder containing wire connector is sometimes used because of (1) its good connection operability, (2) its small connected portion, (3) its large connection strength, and other reasons.

Figure 8A:
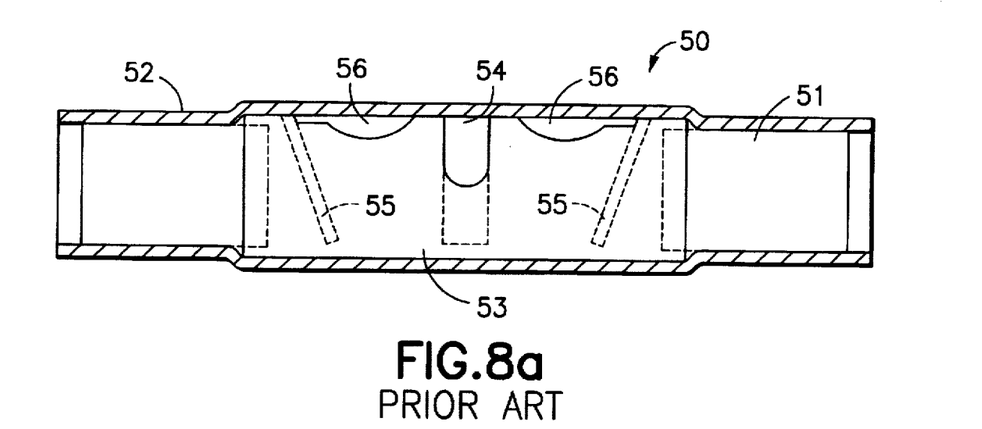
FIGS. 8(a) and (b) are diagrams of a prior art solder containing wire connector.
Figure 8B:
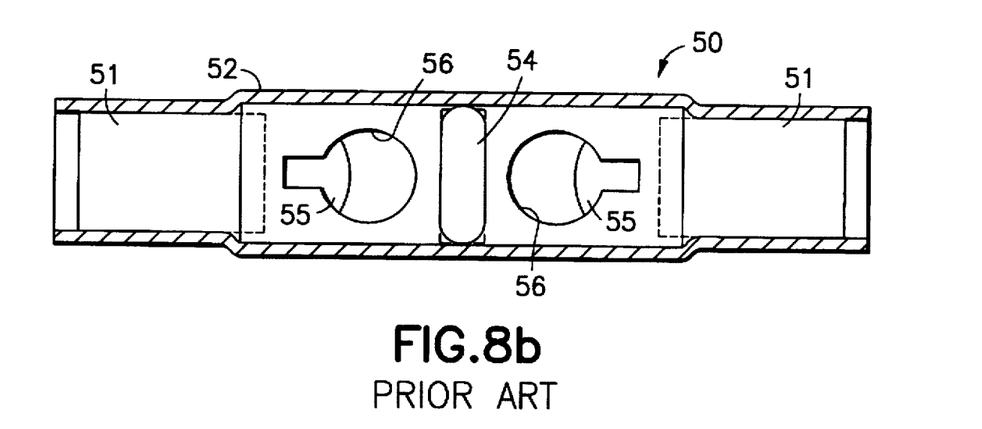

As shown in FIG. 8(a) and 8(b), a solder containing wire connector 50 includes a heat shrinkable tube 52, a metal tube 53, a solder block 54, and wire pressing portions 55. The heat shrinkable tube 52 is formed with annular hot melt resin layers 51 on the inner surfaces of its opposite ends. The metal tube 53 is inserted in a longitudinal center portion of the heat shrinkable tube 52. The solder block 54 is provided in a longitudinal center portion of the metal tube 53. The wire pressing portions 55 having a springy property are suspended from above at the opposite sides of the solder block 54 in the metal tube 53 and form check holes 56 in the metal tube 53. Wires are connected with the solder containing wire connector in the manner as described below.

Figure 9:
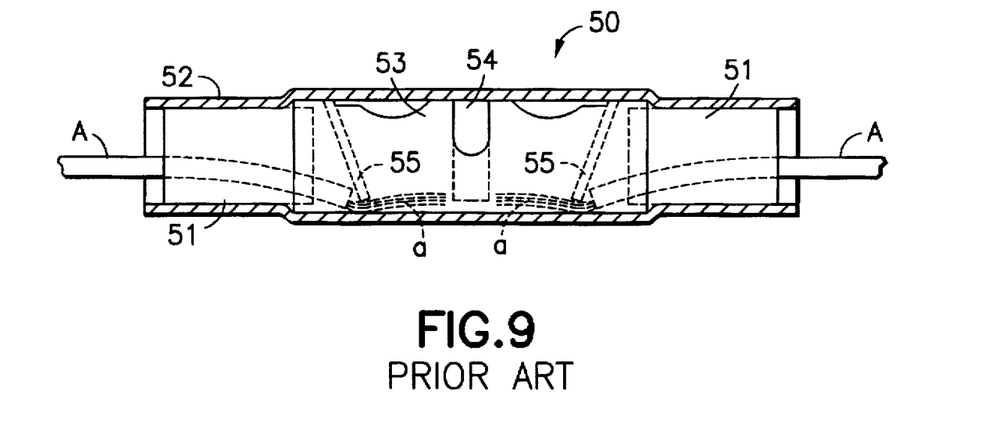
FIGS. 9 and 10 are diagrams showing a prior art wire connecting step when the solder containing wire connector is used.

First, as shown in FIG. 9, wires A each having their insulating sheath peeled off at at least one of their leading ends to expose a core a are inserted into the metal tube 53 through the opposite ends of the heat shrinkable tube 52. The wires A are inserted while pressing the wire pressing portions 55 upward until the cores "a" at their ends reach specified positions near the solder block 54. Since the cores "a" of the wires A are pressed by the corresponding wire pressing portions 55, the wires A are securely retained in this state.

Figure 10:
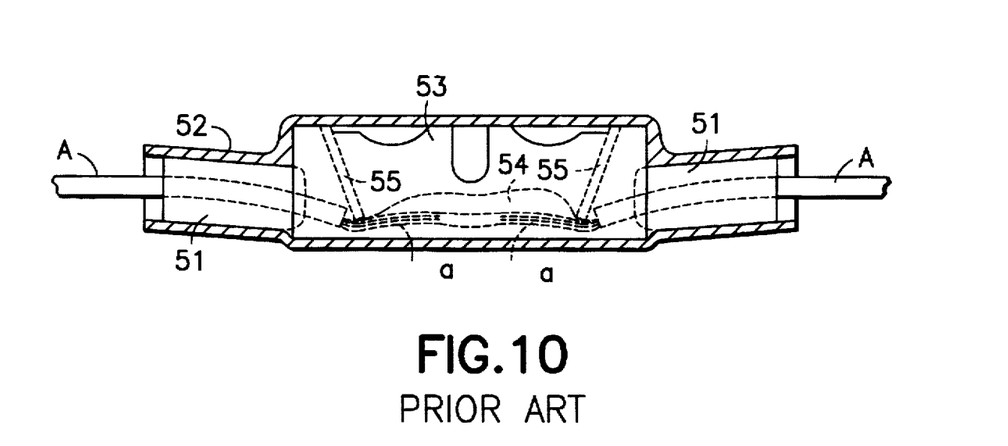

Upon heating the entire solder containing wire connector 50 into which the wires A are inserted, the solder block 54 starts melting, thereby soldering the cores "a" to the inner surface of the metal tube 53 as shown in FIG. 10. As a result, both wires A are electrically and mechanically connected with each other. At this stage, the hot melt resin layers 51 provided at the opposite ends of the heat shrinkable tube 52 start melting to be adhered to the wires A extending from the opposite ends of the metal tube 53, and the heat shrinkable tube 52 shrinks to completely seal the connected portions in the metal tube 53.

There are two types of apparatuses for heating the solder containing wire connector 50: a single type including a contained heater and a conveyor type including an exposed heater.

Figure 11:
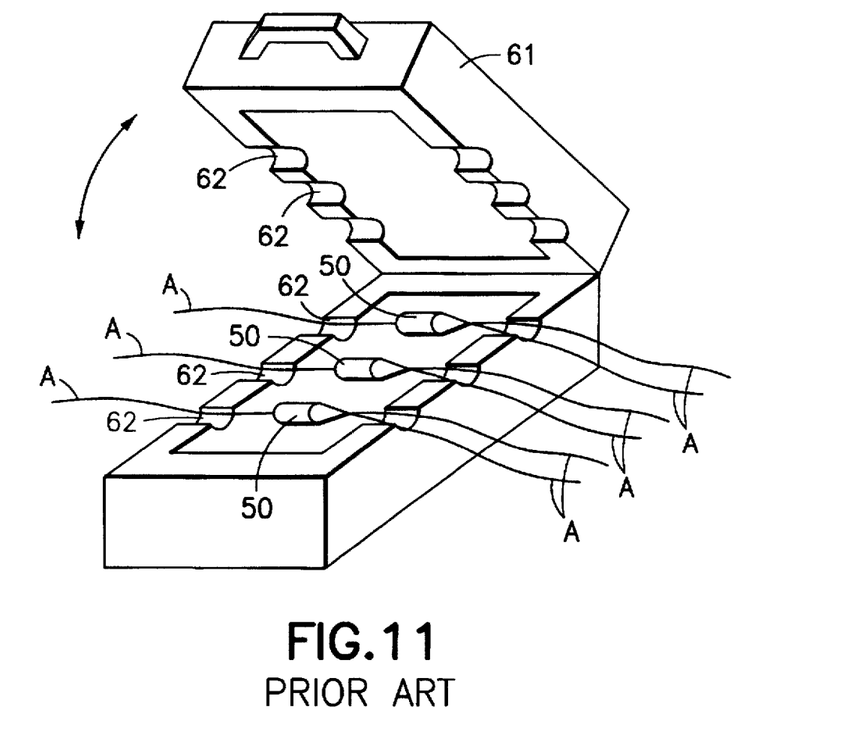
FIG. 11 is a perspective view of a prior art heating apparatus.

An exemplary heating apparatus of single type is shown in FIG. 11. An openable container 61 provided internally with a heater (not shown) is formed with a plurality of grooves 62 for fittably supporting portions of the wires A inserted into the solder containing wire connectors 50. The connectors 50 are set in the container 61 by placing the wire portions along the grooves 62, and are heated by operating the heater after the container 61 is closed.

Figure 12:
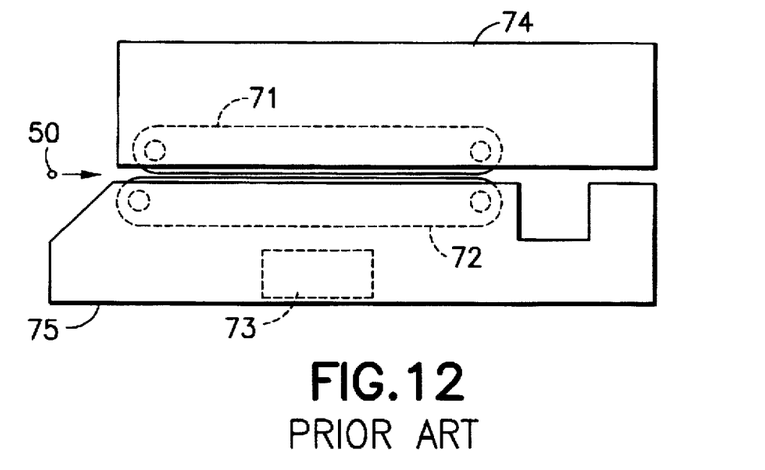
FIG. 12 is a side view of another prior art heating apparatus.
Figure 13:
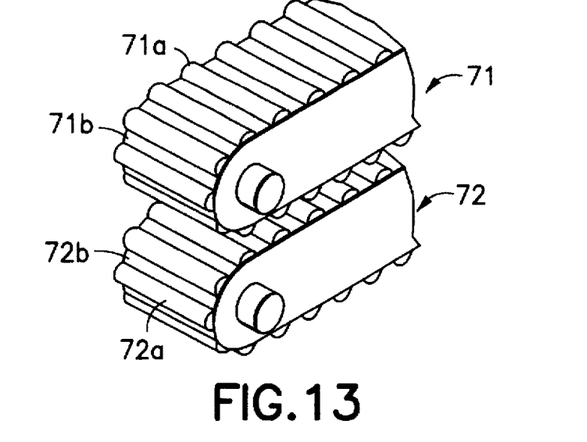
FIG. 13 is a detailed perspective view of a belt conveyor of the another prior art heating apparatus.

On the other hand, an exemplary heating apparatus of conveyor type is shown in FIGS. 12 and 13. This heating apparatus includes upper and lower belt conveyors 71, 72, a heater 73 disposed below the lower belt conveyor 72, and casings 74, 75 for covering the belt conveyors 71, 72 and the heater 73. As shown in FIG. 13, a plethora of grooves 71b, 72b in which the solder containing wire connectors 50 are fitted are formed one after another on the outer surfaces of belts 71a, 72a of the respective belt conveyors 71, 72. The connector 50 is conveyed while being held between the corresponding grooves 71b, 72b of the upper and lower belt conveyors 71, 72. The connector 50 is heated by the heater 73 during conveyance.

With the heating apparatus of single type, the solder containing wire connectors 50 are heated while being housed in the container 61 provided internally with the heater. Since heating can be performed efficiently and uniformly, the connection of the wires and the waterproofness of the connected portions can be advantageously constantly kept at a specified level. However, after the start of heating of the connectors 50 housed in the container 61, an operator has to wait until heating is completed. This waiting period disadvantageously leads to a poor working efficiency.

SUMMARY OF THE INVENTION

This object is solved according to the invention by an apparatus according to claim 1. Preferred embodiments of the invention are subject of the dependent claims.

According to the invention, there is provided an apparatus for heating a wire connection, in particular a connector, comprising:

a plurality of heating units arranged at specified intervals, each comprising a container for housing a content, in particular the wire connection or connector, and heating means for heating the content of the container, conveying means for successively conveying the plurality of heating units along a conveyance path including a loading station for arranging the content, in particular the connection or connector inside the heating unit and an unloading station for taking the content, in particular the connection or the connector out of the heating unit, and controlling means for operating the heating means for a predetermined or predeterminable period while the heating unit is conveyed between the loading station and the unloading station.

Power for the heating means may be delivered through the conveying means by known electrical distribution systems, such as those shown in U.S. Pat. No. 5,449,056, U.S. Pat. No. 5,503,259, U.S. Pat. No. 4,550,231, U.S. Pat. No. 4,428,466, U.S. Pat. No. 4,418,251, U.S. Pat. No. 4,400,592, U.S. Pat. No. 4,375,195, U.S. Pat. No. 4,227,596, U.S. Pat. No. 4,155,435, U.S. Pat. No. 4,372,481, U.S. Pat. No. 3,476,889 and/or U.S. Pat. No. 2,821,146, the disclosures of which are incorporated herein by reference.

According to a preferred embodiment of the invention, the apparatus further comprises a cooling means for cooling in particular the content of the container.

Preferably, the container is formed with an air supply hole and an air release hole for cooling, in particular the content.

Further preferably, the conveyance path also includes a cooling station between the loading station and the unloading station for cooling, in particular the content of the container, wherein the cooling is preferably performed by supplying air through the supply hole formed in the container.

Further preferably, the controlling means operates the heating unit for the predetermined period while the heating unit is conveyed between the loading station and the cooling station.

Further preferably, the cooling means is provided on each heating unit.

According to a further preferred embodiment, the heating unit is a closable heating unit comprising at least two elements connected via hinge means.

Preferably, there is provided a wire for closing the at least two elements by pulling on the wire, preferably wherein the wire is connected on one side with one element and on the other side with a solenoid provided on the other element for releasing the pulling force on the wire, wherein the solenoid is preferably controlled by means of the controlling means.

According to a still further preferred embodiment of the invention, the apparatus further comprises a supplementary control apparatus, the supplementary control apparatus comprising:

- a color image pickup means for picking up a color image of the content, in particular the connection,
- an image extracting means for extracting a predetermined or predeterminable image color component from the color image,
- an image processing means for processing the image color component in order to calculate a defect area of the content, and
- a discriminator means for discriminating whether the content is satisfactory and for outputting a control signal, preferably to the controlling means for operating the heating means.

According to a further embodiment, there is provided an apparatus for heating a solder containing wire connector connected with wires, the connector comprising a heat shrinkable tube, a metal tube inserted in a longitudinal center portion of the heat shrinkable tube, and a solder block provided in a longitudinal center portion of the metal tube, and being used such that, after wires, each having its insulating sheath at its leading end peeled off to expose a core, are inserted into portions of the metal tube at the opposite sides of the solder block, heating is applied to melt the solder block so that the cores of the wires are soldered to the metal tube, thereby establishing an electrical connection between the wires, and to cause the heat shrinkage tube to shrink, thereby adhering the heat shrinkage tube to the wires extending from the metal tube to seal the metal tube, comprising:

- a plurality of closable heating units arranged at specified intervals, each comprising a container for housing the solder containing wire connector into which the wires are inserted, and heating means for heating the connector housed in the container,
- conveying means for successively conveying the plurality of closable heating units along a loop-shaped conveyance path, including a setting station for setting the connector in the closable heating unit and an unloading station for taking the connector out of the closable heating unit, and
- controlling means for operating the heating means for a predetermined period while the closable heating unit is conveyed between the setting station and the unloading station.

Accordingly, upon being set in the closable heating units successively sent at specified intervals, the solder containing wire connectors are successively conveyed to the unloading station after being heated in the respective heating units for the predetermined period.

Preferably, the container of each closable heating unit is formed with a supply hole and a release hole for air for cooling, and the conveyance path further includes a cooling station between the setting station and the unloading station for supplying the air for cooling through the supply hole formed in the container. The controlling means preferably operates the heating means for the predetermined period while the closable heating unit is conveyed between the setting station and the cooling station.

Accordingly, after completion of the heating in the heating units, the solder containing wire connectors are successively conveyed to the unloading station after being cooled by the cooling station.

As described above, in the inventive heating apparatus, upon being set in the closable heating units successively sent at specified intervals, the solder containing wire connectors are successively conveyed to the unloading station after being heated in the respective heating units for the predetermined period. Accordingly, operators engaged in setting the connectors in the heating units and taking them out from the heating units do not have to wait between the setting operations and between the unloading operations, respectively. In other words, working efficiency is good. Further, since the connectors are efficiently and uniformly heated in the closed heating units, the connection of the wires and the waterproofness of the connected portion can be constantly kept at satisfactory level.

Further, in the heating apparatus provided with the cooling station, the solder containing wire connectors are conveyed to the unloading station after being securely cooled. Therefore, the connectors can be efficiently unloaded and can advantageously immediately conveyed to a location of a next production step.

DETAILED DESCRIPTION OF THE PREFERRED EMBODIMENT

Figure 1:
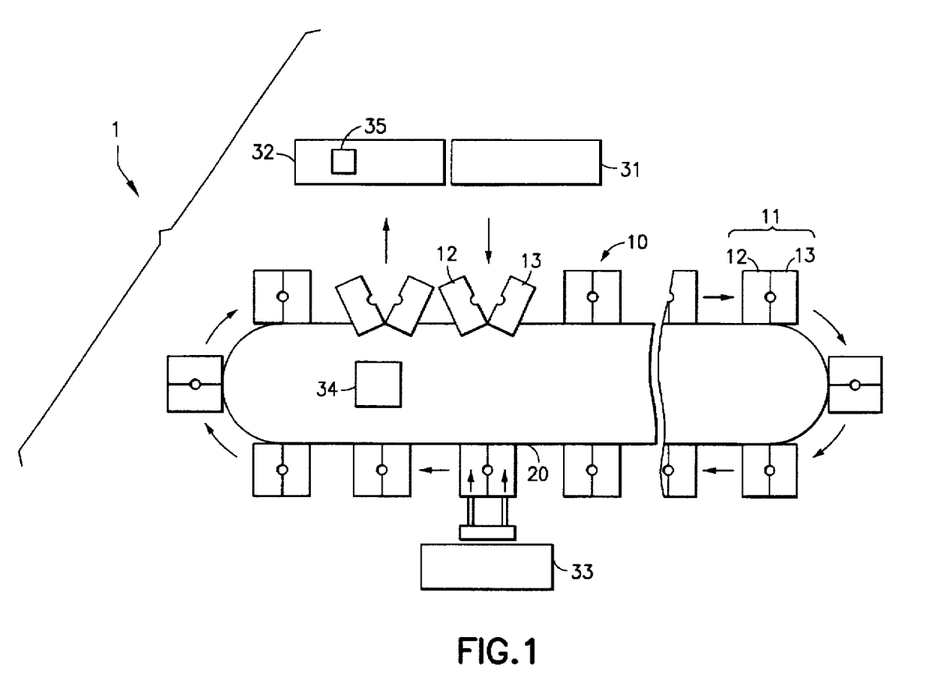
FIG. 1 is a schematic diagram of one embodiment according to the invention.

Hereafter, one embodiment of the invention is described with reference to the accompanying drawings. Since the solder containing wire connector used here is same as the one described under the caption, no description is given thereto. As shown in FIG. 1, a heating apparatus 1 includes a plurality of closable heating units 10 arranged at specified intervals, a conveyor 20 for conveying the heating units 10 along a loop-shaped conveyance path including a loading or setting station 31, an unloading station 32 and a cooling station 33, and a controller 34 for controlling heating of the heating units 10. The unloading station 32 optionally includes a checking apparatus 35.

Figure 2:
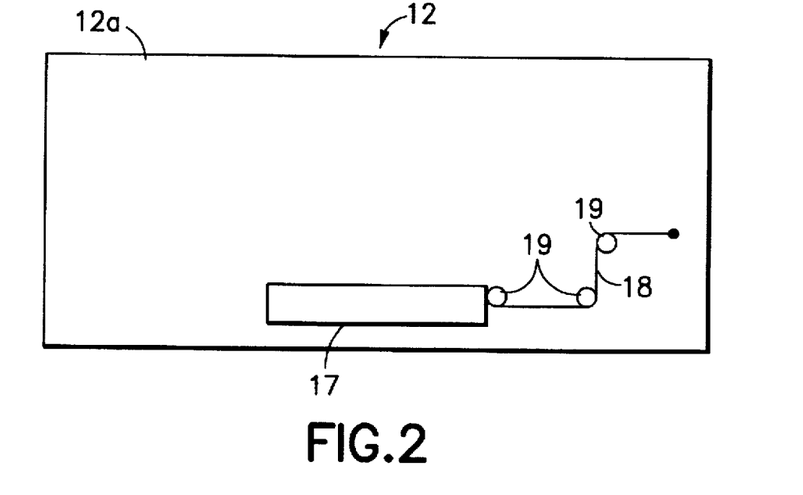
FIG. 2 is a side view of a closable heating unit according to the embodiment.
Figure 3:
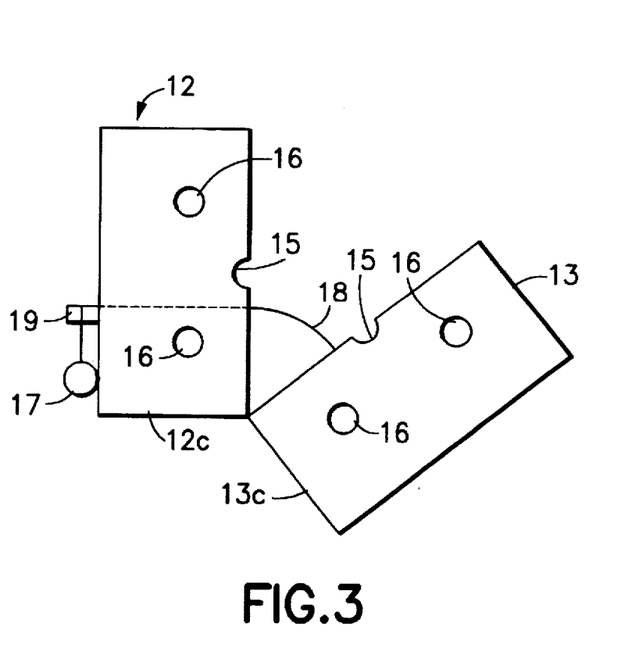
FIG. 3 is a diagram of one end surface of the closable heating unit.

As shown in FIG. 1, each heating unit 10 is such that a rectangular container 11 is divided into two elements 12, 13 in the middle with respect to its widthwise direction and the respective divided elements 12, 13 are openably connected via an unillustrated hinge. One divided element 12 is, as shown in FIGS. 2 and 3, provided with a solenoid 17 mounted on its outer surface 12a and a wire 18. One end of the wire 18 is connected with the solenoid 17 and the other end thereof is guided by guide rollers 19 and connected with the other divided element 13. The divided elements 12 and 13 are opened and closed by pulling the wire 18 toward the divided element 12 and releasing the pulling force by means of the solenoid 17, respectively.

Figure 4:
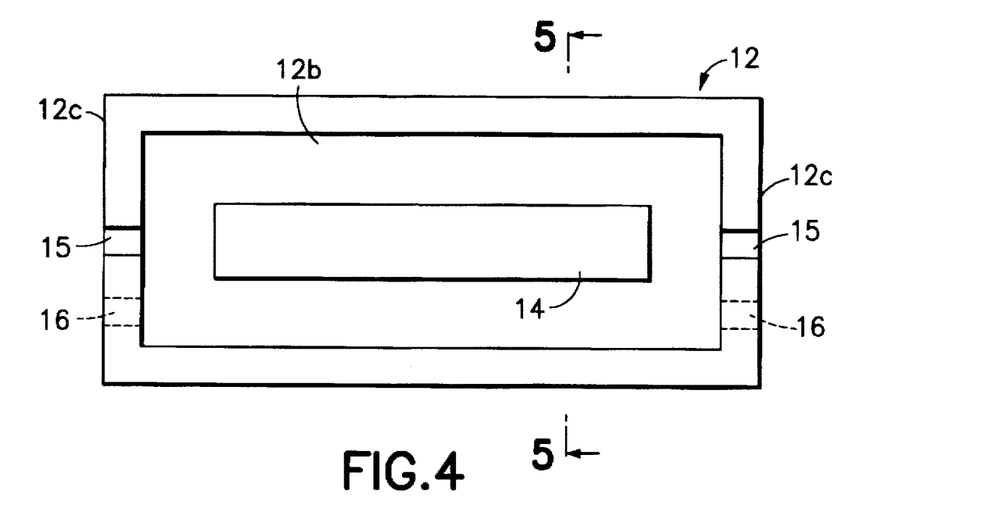
FIG. 4 is an inner side view of one divided element of a container according to the embodiment.
Figure 5:
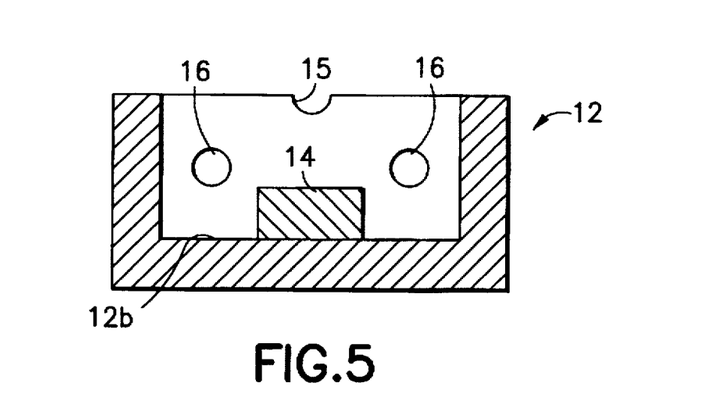
FIG. 5 is a section of the divided element.

As shown in FIGS. 4 and 5, a heater 14 is mounted on an inner surface 12b of the divided element 12. Grooves 15 for accommodating portions of wires A inserted into the connector 50 are formed in the center of a contact surface of each of the divided elements 12, 13.

Two holes 16 for supplying and releasing an air for cooling are formed on each opposite end surface of each of the divided elements 12, 13. The air supplied through the holes 16 formed in surfaces at one end of the divided elements 12, 13 is released through the holes 16 formed in surfaces at the other end thereof. Though not shown, a heat insulating material is adhered to the inner surfaces of the container 11 so as to enhance heating efficiency.

The conveyor 20 is formed by mounting an endless metal belt 21 on gears (not shown) disposed at opposite lateral ends. The metal belt 21 is moved by rotating one gear by means of an unillustrated driving force.

Figure 6:
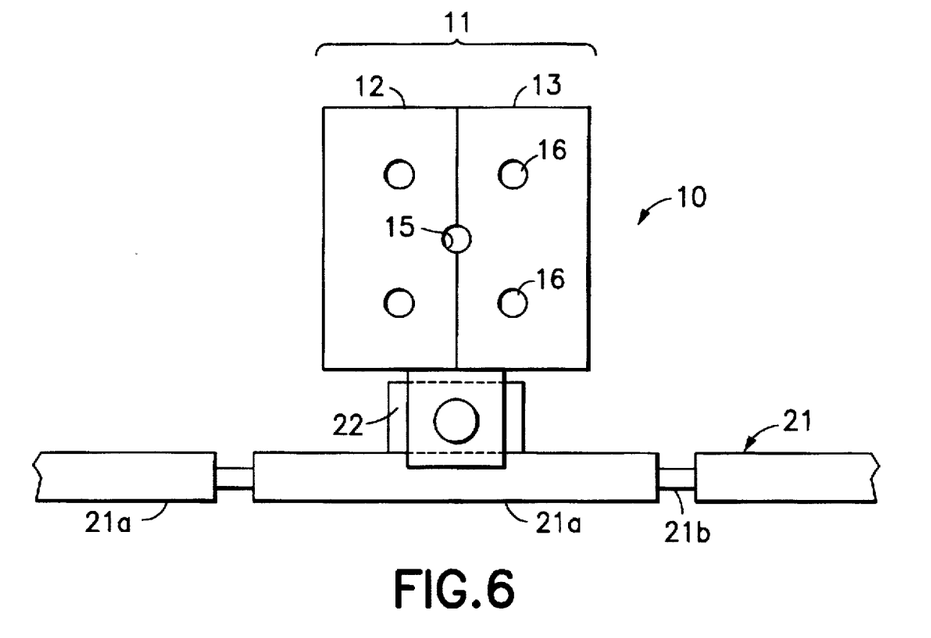
FIGS. 6 and 7 are diagrams showing how the closable heating unit is mounted on a conveyor.
Figure 7:
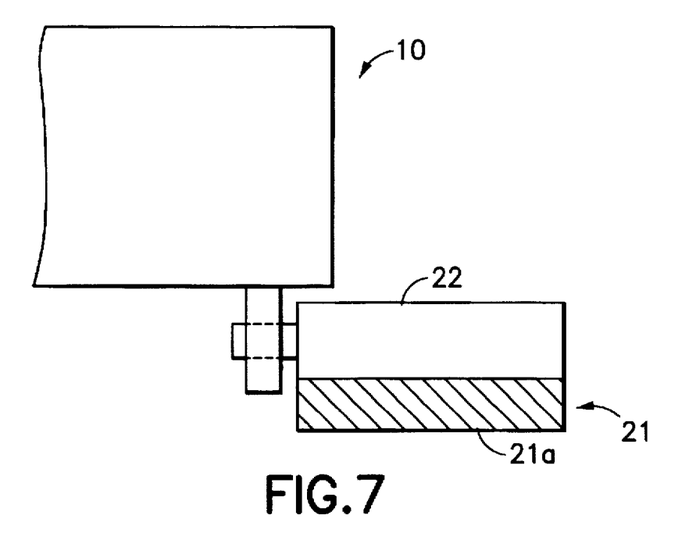

The metal belt 21 is, as shown in FIGS. 6 and 7, such that a plethora or plurality of metal plates 21a are connected via connecting members 21b. Support members 22 for supporting the heating units 10 are secured on the respective metal plates 21a at specified intervals. Accordingly, by mounting the heating units 10 via the support members 22, a plurality of heating units 10 can be secured on the metal belt 21 at specified intervals.

In the heating apparatus 1 thus constructed, after a given heating unit 10 reaches the setting station 31, the solenoid 17 releases the pulling force of the wire 18, thereby opening the container 11. At this stage, after placing the portions of the wires A inserted into the solder containing wire connector 50 in the grooves 15 formed in the divided element 12, an operator operates the solenoid 17 to close the container 11, with the result that the connector 50 is housed in the container 11. Thereupon, the conveyor 20 starts moving to convey the heating unit 10 housing the connector 50 and the next heating unit 10 reaches the setting station 31. The operator repeats the similar operation.

The heating units 10 housing the connectors 50 are conveyed one after another in this way. At the same time the heating unit 10 is sent out from the setting station 31, the controller turns the heater 14 in the heating unit 10 on to heat the housed connector 50. Heating by the heater 14 is continued until the heating unit 10 reaches the cooling station 33, and a solder block 54 in the connector 50 melts and a heat shrinkable tube 52 therein shrinks during this period.

In the cooling station 33, the air for cooling is supplied through the holes 16 formed in one end surface of the container 11 of each heating unit 10, and is released through the holes 16 formed in the other end surface of the container 11. In this way, the connector 50 is cooled.

The heating unit 10 thus cooled is conveyed to the unloading station 32 by the conveyor 20. Upon reaching the unloading station 32, the container 11 opens and an operator takes the connector 50 out of the container 11.

Since the connector 50 thus taken out was cooled after being sufficiently and uniformly heated in the heating unit 10, the connection of the wires A is good and the connected portion has a high waterproof performance.

Accordingly, a period required for the heating unit 10 sent out from the setting station 31 to reach the cooling station 33 needs to be set such that the connector 50 can be sufficiently heated by the heater 14 during this period. A conveying speed of the conveyor 20 and the number of heating units 10 mounted on the conveyor 20 have to be decided in consideration of the above heating period. However, if the conveying speed of the conveyor 20 is considerably reduced in order to assure a sufficient heating period, the operators at the setting station 31 and the unloading station 32 have to wait for a longer period. Thus, in deciding the conveying speed of the conveyor 20, this point also has to be sufficiently considered.

Although the metal belt 21 of the conveyor 20 is moved along a vertical plane in the foregoing embodiment, the invention is not particularly limited to this. The metal belt 21 may be moved along a horizontal plane. Further, the construction of the conveyor 20 itself is not limited to the one described in the foregoing embodiment, either. Any conveyor can be used provided that it is capable of conveying the heating units 10 along a specified loop-shaped conveyance path.

Figure 14:
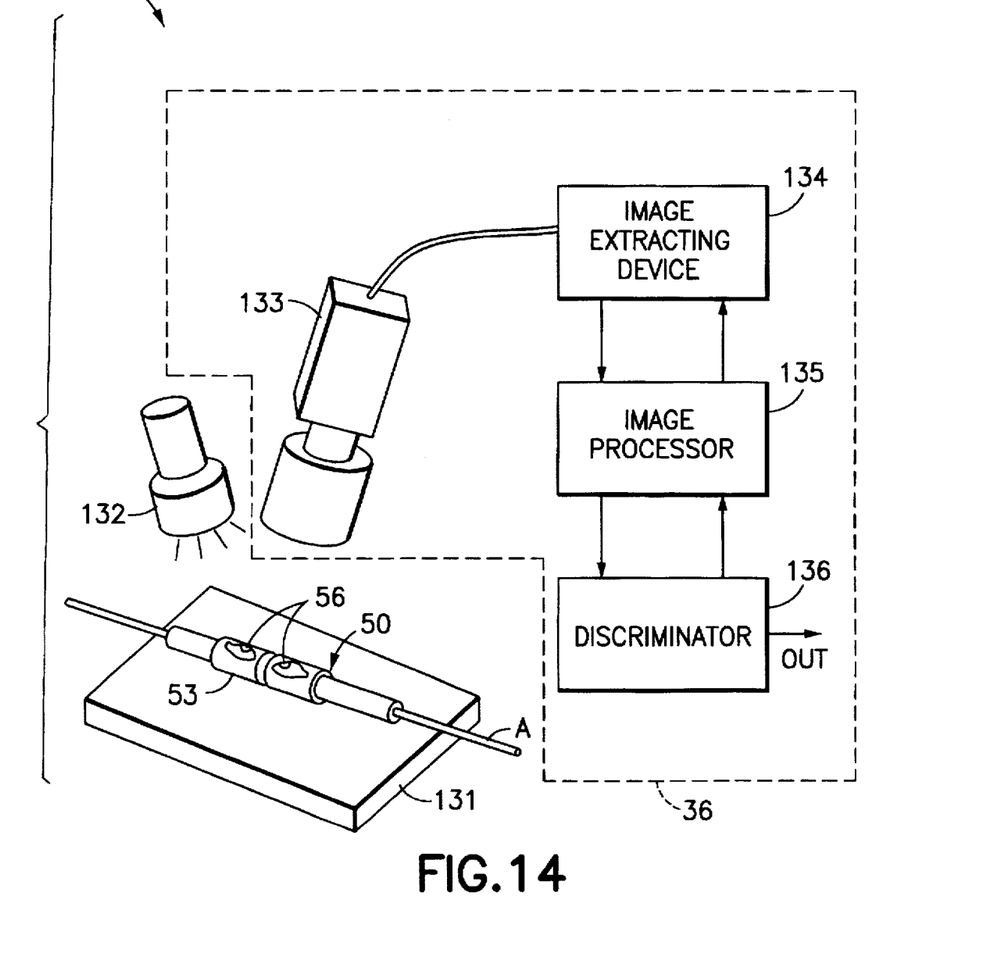
FIG. 14 is a perspective view of the supplementary control apparatus relying upon color images of the connector.

FIG. 14 shows a connection checking apparatus 35 that may be used in association with the unloading station 32 of the heating apparatus 1 of FIG. 1. Specifically, the checking apparatus 35 includes a plate-like checking table 131 on which a connector 50 connected with wires A is placed, an illuminating device 132 for projecting light upon the connector 50 placed on the checking table 131. The checking apparatus 35 further includes a supplementary control 36 which includes a color image pickup 133 for picking up a color image of the connector 50 on the checking table 131, an image extracting device 134, an image processor 135 and a discriminator 136. The image extracting device 134 is electrically connected with the color image pickup 133 and is adapted to extract e.g. by means of filtering and/or masking a component image of a desired color from the color image picked up by the pickup 133. The image processor 136 calculates an area of the desired color based on the extracted component image. The discriminator 136 compares the area calculated by the image processor 135 with a predetermined threshold value and determines whether or not the connection of the wires A is satisfactory.

Figure 15:
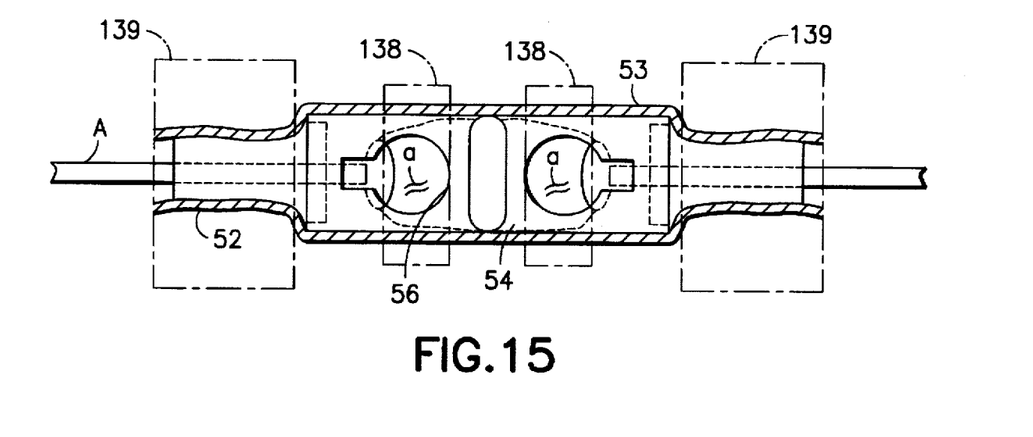
FIG. 15 is a top plan view of a connector showing discrete windows subject to color image inspection.

The checking method adopted by the above checking apparatus is described below, with reference to FIG. 14 and 15. The connector 50 connected with the wires A is placed on the checking table 131 such that the check holes 56 of a metal tube 53 of the connector 50 face upward, i.e. face the color image pickup 133. In other words, the connector 50 is placed such that the color image pickup 133 can pick up an image of a molten solder 54 or cores "a" exposed from or not covered by the molten solder 54 as shown in FIG. 15.

The color image pickup 133 picks up an image of the connector 50. At this stage, the color image of the connector 50 used to extract the component color image or image color component to be described later and a binary image of the connector 50 are obtained and stored, for example, in a memory provided in the image extracting device 134. The contour of the connector 50 is obtained based on the obtained binary image, and soldering checking windows 138 (first area) and hot melt checking windows 139 (second and third areas) as shown in FIG. 15 are set. A pair of soldering checking windows 138 are set in areas at least partly including the check holes 56 of the metal tube 53 as indicated by phantom line in FIG. 15, whereas a pair of hot melt checking windows 139 are set in areas at least partly including molten hot melts 52.

The heaters 14 for heating the connectors 50 may be controlled based on the thus obtained determination results. Specifically, the data concerning the respective determination results are transferred to the heater controller 34. If the soldering by the solder 16b is determined to be unsatisfactory in the first determination step, it means insufficient heating.

Accordingly, the heater controller increases a heating temperature of the heater or prolongs a heating time thereof (first automatic heating control step). If the softening of the hot melts 52 is determined to have been unsatisfactory in the second determination step, it also means insufficient heating. Accordingly, in this case as well, the heater controller 34 increases the heating temperature of the heater or prolongs the heating time thereof (second automatic heating control step). Further, if the connector 50 is determined to be carbonized in the third determination step, it means excessive heating. Accordingly, the heater controller 34 decreases the heating temperature of the heater or shortens the heating time thereof (third automatic heating control step).

A next connector heating operation is suitably adjusted by automatically controlling the heating temperature and the heating time of the heater based on the respective determination results by means of the heater controller 34. This effectively prevents a defective connection of wires.

LIST OF REFERENCE NUMERALS

1 . . . Heating Apparatus
10 . . . Closable Heating Unit
11 . . . Container
14 . . . Heater
16 . . . Hole
20 . . . Conveyor
21 . . . Metal Belt
31 . . . Setting Station
32 . . . Unloading Station
33 . . . Cooling Station
34 . . . Controller
35 . . . Checking Apparatus
50 . . . Solder Containing Wire Connector

What is claimed is:

1. An apparatus for heating a wire connector, comprising:
a plurality of heating units (10) arranged at specified intervals, each comprising a container (11) for housing a wire connector (50), and heating means (14) for heating the wire connector (50) in the container (11),
conveying means (20) for successively conveying the plurality of heating units (10) along a conveyance path including a loading station (31) for arranging the connector (50) inside the heating unit (10) and an unloading station (32) for taking the connector (50) out of the heating unit (10), and
controlling means for operating the heating means (14) for a predeterminable period while the heating unit (10) is conveyed between the loading station (31) and the unloading station (32).

2. An apparatus for heating a wire connector, comprising:
a plurality of heating units (10) arranged at specified intervals, each comprising a container (11) for housing a wire connector (50), and heating means (14) for heating the wire connector (50) in the container (11),
a cooling means for cooling interior portions of the container (11),
conveying means (20) for successively conveying the plurality of heating units (10) along a conveyance path including a loading station (31) for arranging the connector (50) inside the heating unit (10) and an unloading station (32) for taking the connector (50) out of the heating unit (10), and
controlling means for operating the heating means (14) for a predeterminable period while the heating unit (10) is conveyed between the loading station (31) and the unloading station (32).

3. An apparatus according to claim 2, wherein the container (11) is formed with an air supply hole (16) and an air release hole (16) for cooling the interior portions of the container.

4. An apparatus according to claim 3, wherein the conveyance path further includes a cooling station (33) between the loading station (31) and the unloading station (32) for cooling interior portions of the container (11).

5. An apparatus according to claim 4, wherein the cooling is performed by supplying air through the supply hole (16) formed in the container (11).

6. An apparatus according to claim 4, wherein the controlling means operates the heating means (14) for the predetermined period while the heating unit (10) is conveyed between the loading station (31) and the cooling station (33).

7. An apparatus according to claim 2, wherein the cooling means is provided on each heating unit (10).

8. An apparatus for heating a wire connector, comprising:
a plurality of closable heating units (10) arranged at specified intervals, each said heating unit comprising at least two elements (12, 13) hingedly connected to one another, a container (11) for housing a wire connector (50), and heating means (14) for heating the wire connector (50) in the container (11),
conveying means (20) for successively conveying the plurality of heating units (10) along a conveyance path including a loading station (31) for arranging the connector (50) inside the heating unit (10) and an unloading station (32) for taking the connector (50) out of the heating unit (10), and
controlling means for operating the heating means (14) for a predeterminable period while the heating unit (10) is conveyed between the loading station (31) and the unloading station (32).

9. An apparatus according to claim 8, wherein there is provided a wire (18) for closing the at least two elements (12, 13) by pulling on the wire (18).

10. An apparatus according to claim 9, wherein the wire (18) is connected on one side with one element (13) and on the other side with a solenoid (17) provided on the other element (12) for releasing the pulling force on the wire (18), wherein the solenoid (17) is preferably controlled by means of the controlling means.

11. An apparatus for heating a wire connector, comprising:

a plurality of heating units (10) arranged at specified intervals, each comprising a container (11) for housing a wire connector (50), and heating means (14) for heating the wire connector (50) in the container (11), conveying means (20) for successively conveying the plurality of heating units (10) along a conveyance path including a loading station (31) for arranging the connector (50) inside the heating unit (10) and an unloading station (32) for taking the connector (50) out of the heating unit (10), controlling means for operating the heating means (14) for a predeterminable period while the heating unit (10) is conveyed between the loading station (31) and the unloading station (32), and a supplementary control apparatus, the supplementary control apparatus comprising:

a color image pickup means for picking up a color image of the content, in particular the connection, an image extracting means for extracting a predetermined or predeterminable image color component from the color image, an image processing means for processing the image color component in order to calculate a defect area of the content, and a discriminator means for discriminating whether the content is satisfactory and for outputting a control signal, preferably to the controlling means for operating the heating means (14).

* * * * *